United States Patent
Leise, Jr.

(10) Patent No.: US 9,827,146 B2
(45) Date of Patent: Nov. 28, 2017

(54) MANUFACTURING METHOD FOR WOUND DRESSINGS

(75) Inventor: Walter F Leise, Jr., Bradenton, FL (US)

(73) Assignee: Sarasota Medical Products, Inc., Sarasota, FL (US)

( * ) Notice: Subject to any disclaimer, the term of this patent is extended or adjusted under 35 U.S.C. 154(b) by 1355 days.

(21) Appl. No.: 13/331,295

(22) Filed: Dec. 20, 2011

(65) Prior Publication Data

US 2013/0158458 A1   Jun. 20, 2013

(51) Int. Cl.
*A61G 13/12* (2006.01)
*A61F 13/02* (2006.01)
*B32B 37/12* (2006.01)
B32B 37/00 (2006.01)
B32B 38/00 (2006.01)
A61F 13/00 (2006.01)

(52) U.S. Cl.
CPC ...... *A61F 13/0279* (2013.01); *A61F 13/0289* (2013.01); *B32B 37/1284* (2013.01); *A61F 2013/00697* (2013.01); *A61F 2013/00748* (2013.01); *B32B 37/0053* (2013.01); *B32B 38/0004* (2013.01); *B32B 2317/12* (2013.01); *B32B 2556/00* (2013.01); *Y10T 156/1074* (2015.01)

(58) Field of Classification Search
CPC .............. A61F 13/0203; A61F 13/0276; A61F 2013/00868; A61F 13/02; A61L 15/58; A61L 15/26; A61B 18/1492; A61B 2017/00243; A61B 2018/00392; A61B 2017/00247; A61B 17/00234

USPC .................... 53/450, 553; 602/900
See application file for complete search history.

(56) References Cited

U.S. PATENT DOCUMENTS

| | | | |
|---|---|---|---|
| 3,339,546 A | 9/1967 | Chen | |
| 4,284,703 A * | 8/1981 | Inoue | G03F 7/346 430/142 |
| 4,767,405 A | 8/1988 | Lokken | |
| 4,867,748 A | 9/1989 | Samuelsen | |
| 5,133,821 A | 7/1992 | Jensen | |
| 5,254,447 A * | 10/1993 | Meyer | G03C 1/76 156/230 |
| 5,626,866 A * | 5/1997 | Ebert | A61K 9/7061 424/447 |
| 5,716,475 A * | 2/1998 | Botten | A61F 5/443 156/219 |
| 5,758,660 A | 6/1998 | Lokken | |
| 5,792,090 A | 8/1998 | Ladin | |
| 5,935,363 A | 8/1999 | Gilman et al. | |
| 6,093,276 A | 7/2000 | Leise, Jr. et al. | |
| 6,171,985 B1 * | 1/2001 | Joseph | A61L 15/585 428/316.6 |
| 6,309,500 B1 * | 10/2001 | Jensen | A61F 13/00987 156/220 |

(Continued)

*Primary Examiner* — Ophelia A Hawthorne
(74) *Attorney, Agent, or Firm* — Quarles & Brady LLP (57) ABSTRACT

A wound dressing having a thin barrier layer of soft, pliant adhesive material with a flexible cover layer extending along one side of the adhesive layer and a removable release sheet on the opposite side is disclosed. The adhesive material has a center and border surrounding the center such that the adhesive is contoured. A method for making the contoured dressing using a gear pump and a laminating roller having a predetermined softness and firmness is also disclosed.

20 Claims, 6 Drawing Sheets

(56) References Cited

U.S. PATENT DOCUMENTS

6,626,878 B1 * 9/2003 Leisner .................. A61F 5/443
  604/332
2005/0276965 A1 * 12/2005 Etchells ..................... 428/314.4

* cited by examiner

FIG. 6

MANUFACTURING METHOD FOR WOUND DRESSINGS

BACKGROUND OF THE INVENTION

Field of the Invention

This present invention relates to a contoured dressing and a method of making the contoured wound dressing. The method is substantially a continuous in-line method for making a wound dressing.

Description of the Prior Art

Adhesive skin barriers are widely known in the medical field for use in ostomy faceplates, wound dressings, and skin-contacting gaskets or liners of various shapes and sizes, all of which may be generally referred to as hydrocolloid-containing wafers or dressings. Hydrocolloid dressings have a layer of a soft, pliant adhesive material which has both dry and wet tack. It contains a dispersion of hydrocolloid particles capable of absorbing aqueous fluids and of swelling as the absorption takes place. One side of the wafer is covered with a protective film. The opposite side of the barrier layer is protected until use by a release sheet of siliconized paper or other suitable material.

Generally, making a contoured wafer involves a number of steps including: 1) extrusion or injection of a layer of adhesive onto a web; 2) compression of the adhesive into the desired shape and contour; 3) laminating the contoured wafer with a cover film and/or a release sheet; and 4) cutting the dressing from the web. The order of the steps may be different depending on the manufacturing process, however, the goal is to efficiently and cost effectively produce a wound dressing. Several patents discuss methods of making wound dressings or bandages, including U.S. Pat. No. 3,339,546 to Chen; U.S. Pat. No. 4,867,748 to Samuelson; U.S. Pat. No. 5,133,821 to Jensen; U.S. Pat. No. 5,716,475 to Botten et al.; U.S. Pat. No. 5,935,363 to Gilman et al.; U.S. Pat. No. 6,093,276 to Leise; Jr., et al. and U.S. Pat. No. 6,309,500 to Jensen et al. Chen '546 discusses a method of mixing the hydrocolloid dough, rolling it through a press for uniformity, flattening with a hydraulic press then covering it with a polyethyelene film. Samuelson '748 discusses a flat press and die casting method for creating a dressing with a beveled edge. Jensen '821 discloses a two step process comprising extrusion of the hydrocolloid followed by compression into the desired contour using a roller having pockets to create the shape. Botten '475 discloses a method using injection and compression molding operation wherein the platen has a mold on its surface. Gilman '363 describes a method of making a contoured hydrocolloid wound dressing using a contoured roller wherein at least two of the steps of contouring and cutting are combined. Leise '276 discloses an in-line operation in which the assembling procedures are integrated with the molding, forming, cutting and other parts-making operations to provide a continuity of automated steps. Jensen '500 discloses and claims a method of manufacturing a wound dressing using a contouring and lamination station, a delaminating station, a driving station and a cutting station. These patents use extrusion and/or injection and compression techniques to form the hydrocolloid as well as a mold for forming the shape. Other than Chen '546, each of the processes have some form of automation; however, each of the processes remains time intensive and costly, particularly since a large amount of the adhesive and the protective cover film and release sheet webbing are discarded as waste.

The required successive processing steps make the manufacturing of wound dressings more complex and time intensive. Additional problems involve keeping the freshly-extruded or injected barrier material from sticking to the contouring roller. The wastage of the adhesive, which is generally expensive, and the cover and release sheet webbing makes the process more expensive. The present invention eliminates these issues.

The present invention uses a gear pump to deposit the adhesive. The adhesive, which is preferably heated, is deposited in a predetermined shaped and thickness onto a protective release paper. The deposited adhesive is then laminated with a protective cover film using a roller that has a predetermined softness and firmness. During the laminating step, the edges of the adhesive are feathered to infinity to form a contoured dressing having a center and a border edge. The fully formed contoured dressing is then cut and packaged. There is no wasting of adhesive, film cover webbing or release sheet webbing, which makes the process more cost effective. There is no need for multiple molds in various shapes and sizes as the adhesive is deposited in the desired shape and the laminating roller completes the contouring. The adhesive does not stick to the roller as the laminating roller applies the film cover on the adhesive as it irons the adhesive. The process is also continuous as the gear pump deposits the adhesive and the roller laminates the adhesive while the silicone release web is moving. This manufacturing method fabricates dressings having various shapes and sizes at high rates of speed in a cost effective and energy efficient manner. The present invention provides an economical method for producing a wound dressing.

SUMMARY OF THE INVENTION

It is an object of the present invention to provide a method for making a wound dressing or bandage in a substantially continuous fashion, while eliminating the need for extrusion of the adhesive and avoiding sticking of the adhesive to the laminating roller. In the present invention, the adhesive is deposited in a predetermined shaped and thickness onto a protective release paper using a gear pump. The adhesive which is preferably heated, is deposited then laminated with a protective cover film using a roller with a predetermined firmness under a predetermined pressure. During the laminating step, the edges of the adhesive are feathered to infinity to form a contoured dressing having a center and a border edge. This manufacturing method, using a gear pump to deposit a predetermined amount and shape of adhesive and a laminating roller of predetermined firmness under a predetermined pressure provides a means of fabricating dressings having various shapes and sizes at high rates of speed in a cost effective and energy efficient manner.

In the present invention, the adhesive is deposited in a predetermined shaped, which eliminates waste of the adhesive that results from the cutting and trimming process that is traditionally used. The adhesive is also deposited in a predetermined thickness. The adhesive, in its predetermined shape and thickness, is deposited onto a protective release paper using an acceptable dispensing method such as a gear pump. There is no need for compression into the desired thickness, die cutting or roller molding to create the shape of the adhesive as the shape and thickness are determined by the nozzle of the gear pump and the adhesive is deposited on the web in its desired form. The adhesive, which is on the protective silicone web, is then laminated with a protective film using a laminating roller. The laminating roller, made of foam, silicone rubber, or other suitable material, has a predetermined firmness between 10 and 90 shore A. The adhesive does not stick to the laminating roller as the laminating roller applies the film cover on the adhesive as it irons the adhesive since the film provides a protective barrier. During the ironing, the edges of the adhesive are feathered to infinity to form a contoured dressing having a center and a border edge that is thinner in depth than the center. In a final step, the dressing is cut and packaged. The cutting step is more cost efficient than other methods as the dressing has already been shaped and there is no wastage of adhesive, cover web, or release web.

The manufacturing method of the present invention provides a substantially in-line process for making a contoured adhesive wound dressing. The manufacturing method substantially reduces the energy and the time required to contour a wound dressing or bandage at it eliminates steps. The method of the present invention is also cost effective as it eliminates wastage.

Other features, objects, and advantages of the invention will become apparent from the specification and drawings.

DETAILED DESCRIPTION OF THE INVENTION

Figure 5A:
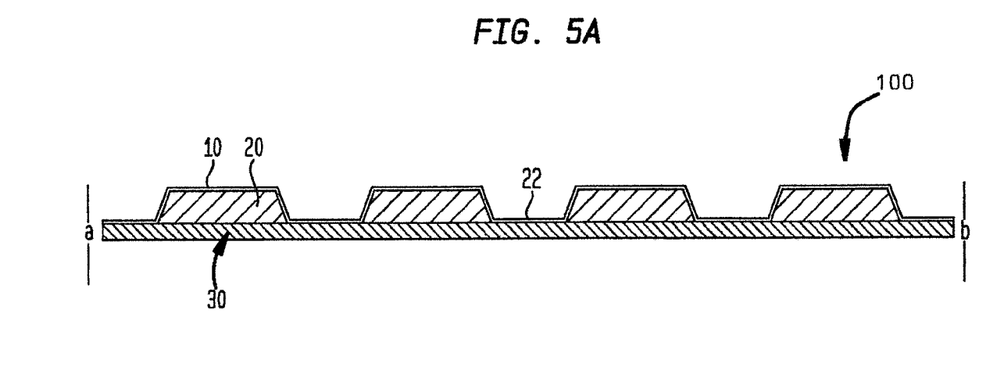
FIG. 5A is a cross section of the formed dressing prior to cutting taken generally along the lines 5A-5A of FIG. 4.
Figure 5B:
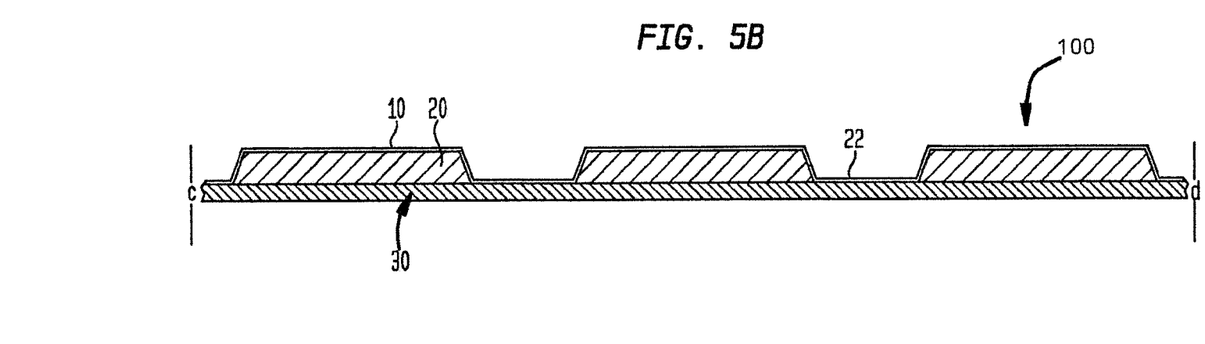
FIG. 5B is a cross section of the formed dressed prior to cutting taken generally along the lines 5B-5B of FIG. 4.
Figure 6:
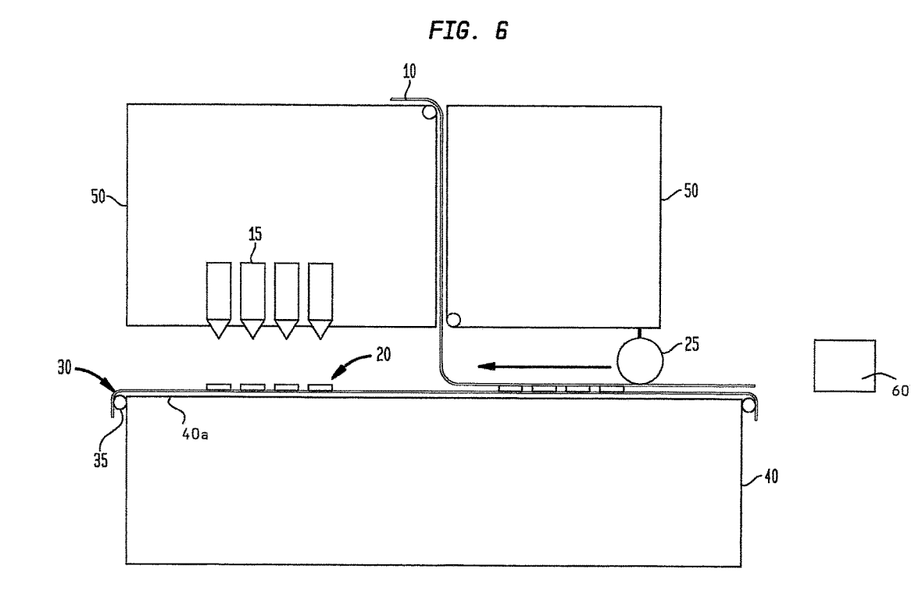
FIG. 6 depicts a machine for making the dressing.

The present invention provides a method for making a wound dressing or bandage comprising the steps of depositing an adhesive (20) in a predetermined shaped and thickness onto a protective release paper web or sheet (30) using a gear pump (15), laminating the deposited adhesive (20) with a protective cover film (10) using a laminating roller (25) with a predetermined firmness to form a bandage or wound dressing (100) as shown in FIG. 6. As shown in FIGS. 5A and 5B, the wound dressing (100) comprises the protective cover film (10), an adhesive wafer comprising the adhesive (20) and the release sheet (30), which is cut after its formation then packaged.

Figure 1:
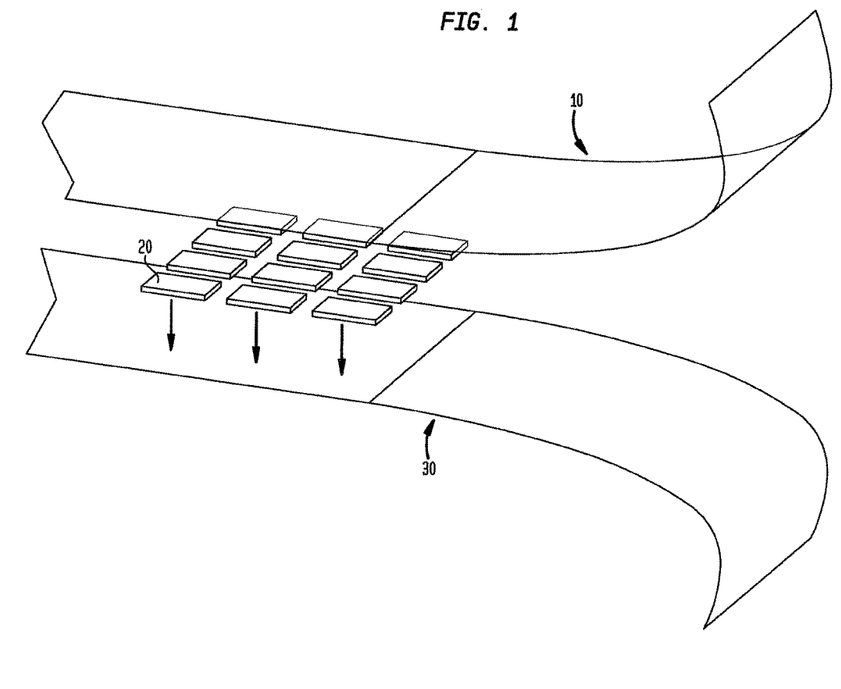
FIG. 1 is a perspective view of the adhesive being sandwiched between the release paper and the cover film without the roller.

As shown in FIG. 6, the adhesive (20) is deposited by a gear pump (15). The adhesive (20) used in the present invention is preferably heated when deposited onto the release paper web (30). The adhesive (20) is delivered through the gear pump (15), or other suitable means, in a predetermined thickness and shape onto a web of protective release paper (30). The measured quantities are formed with a nozzle onto the protective release web (30) that is removably supported on a horizontal upper surface (40a) of a horizontal lower table or platen member (40). As shown in FIG. 1, the adhesive (20) is deposited in a grid in as many units as are feasible on the release paper web (30) given the desired shape and size. As the shape and thickness are predetermined and the adhesive (20) is deposited on the web (30) in its desired form, there is no need for compression into the desired thickness, die cutting, or roller molding to create the shape of the adhesive.

Figure 2:
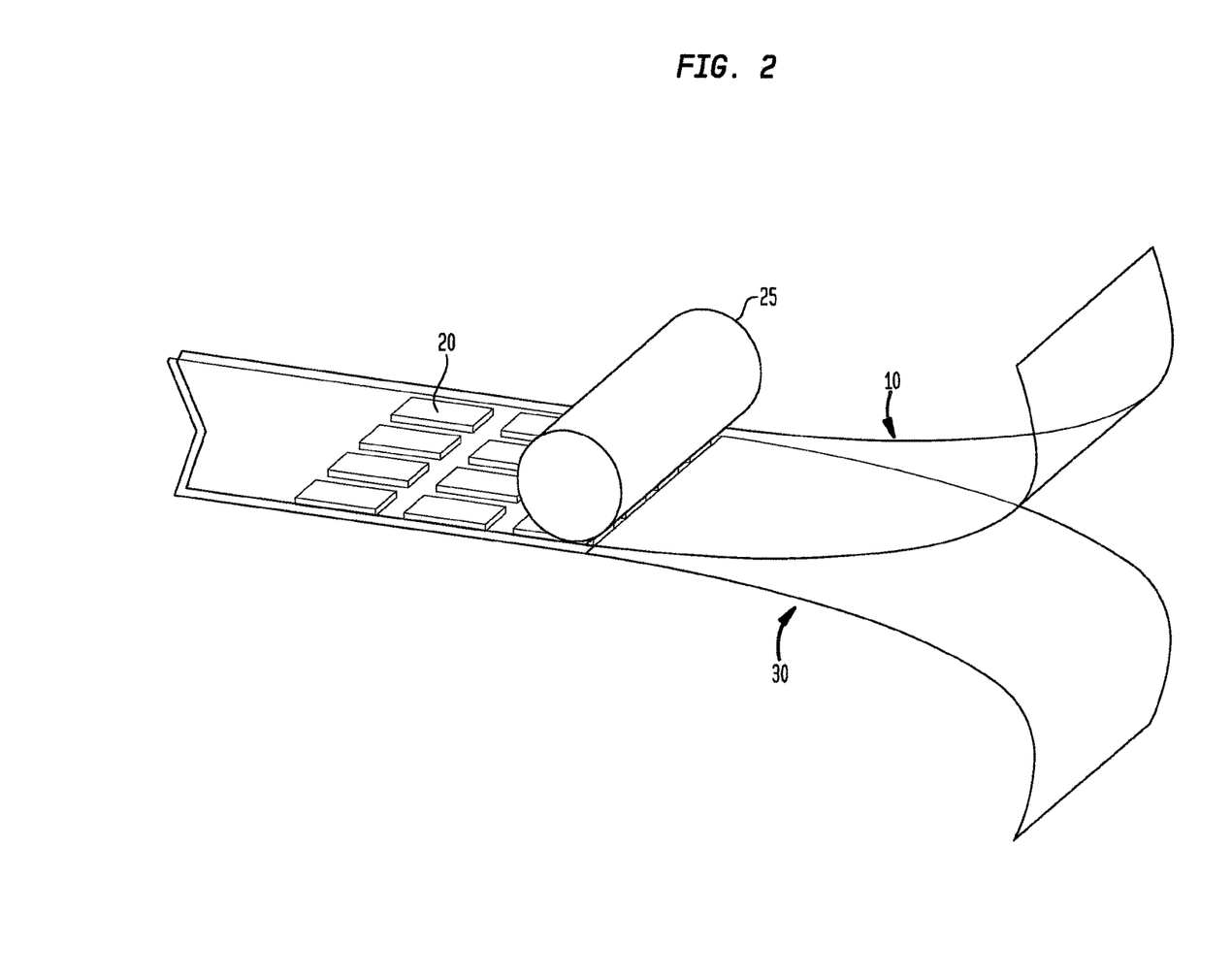
FIG. 2 is a perspective view of the adhesive being sandwiched between the release paper and the cover film with the roller at the beginning prior to feathering of the wafers.
Figure 3:
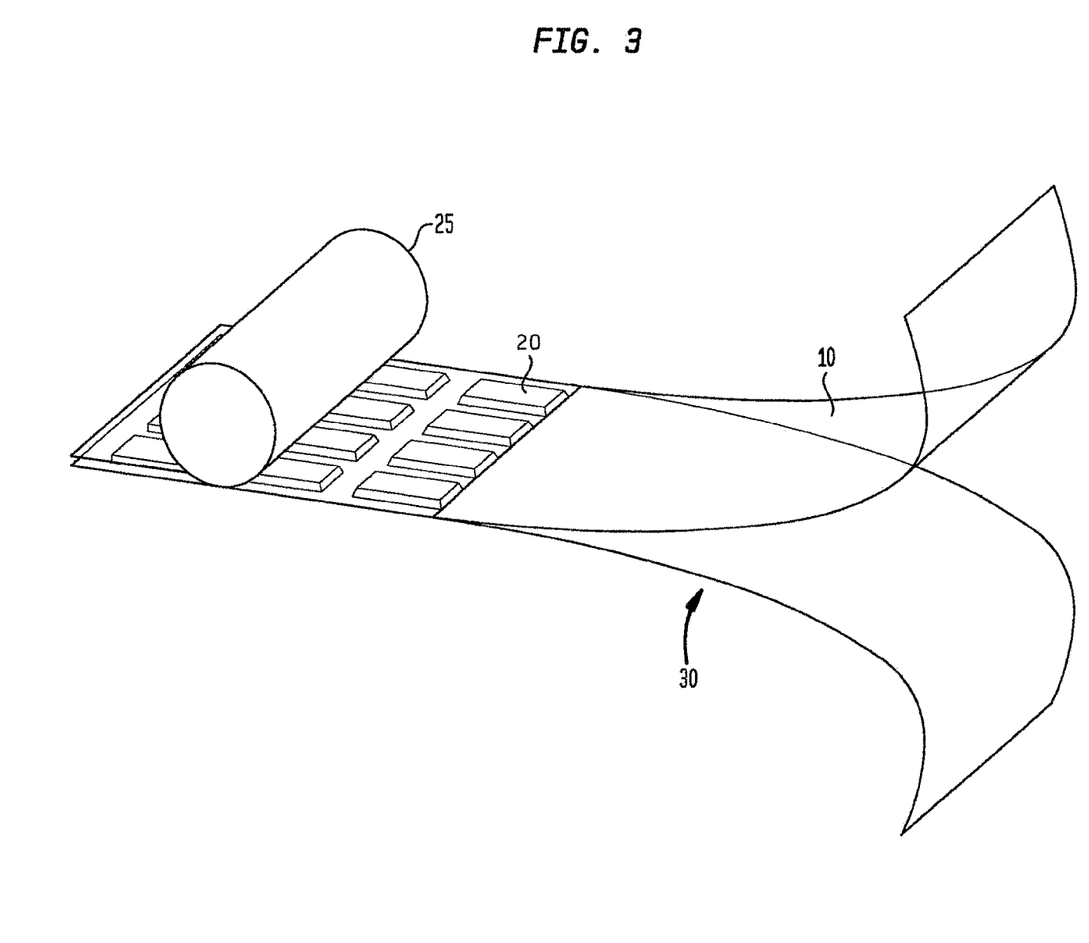
FIG. 3 is a downstream perspective view of the adhesive being sandwiched between the release paper and the cover film during feathering of the wafer.
Figure 4:
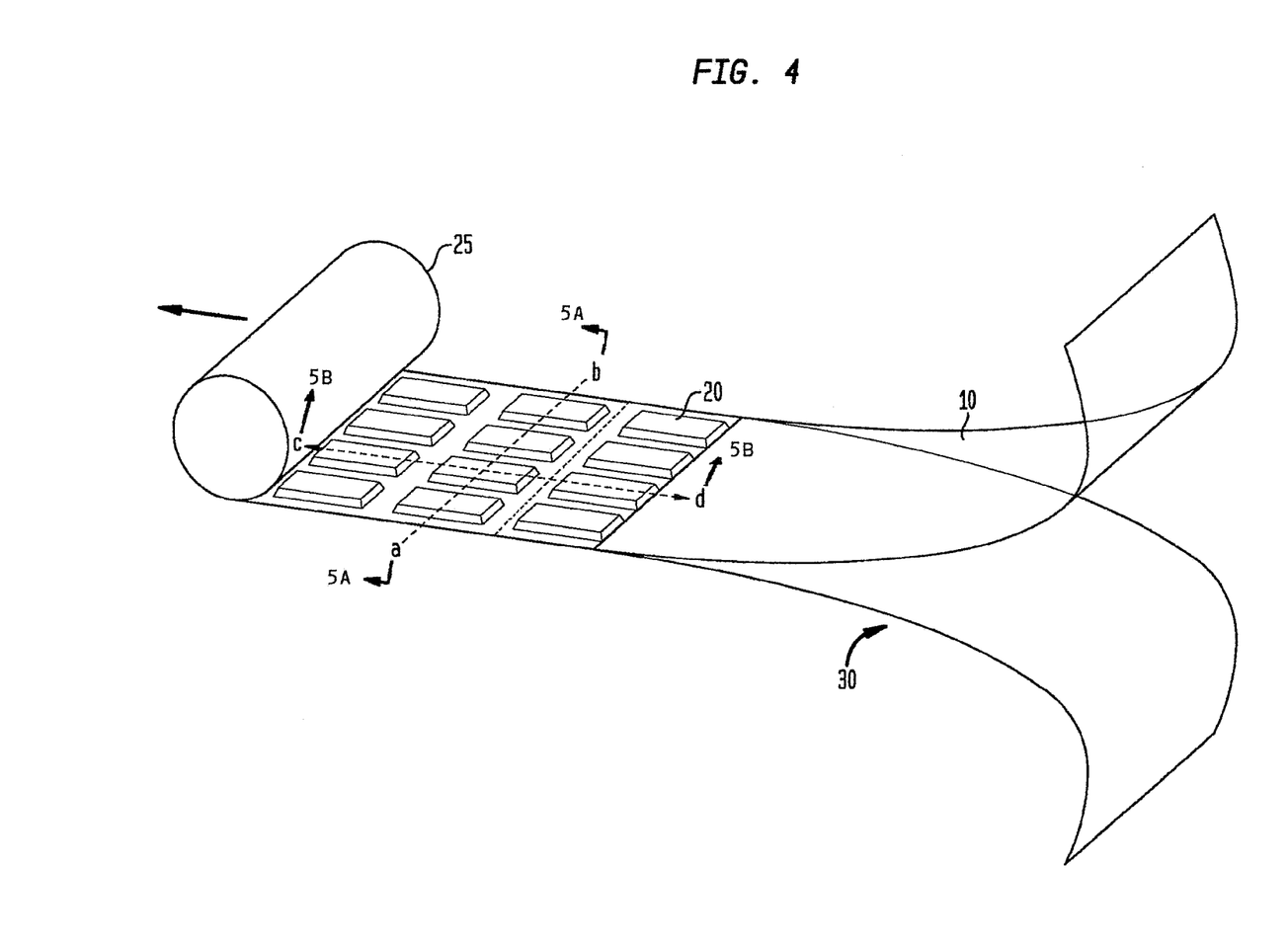
FIG. 4 is a perspective view of the adhesive sandwiched between the release paper and the cover film with after feathering of the wafer.

As shown in FIGS. 2 and 3, the adhesive (20), which is deposited on the protective release silicone web (30), is then laminated with the protective cover (10) using the laminating roller (25). The laminating roller (25), made usually of foam, silicone rubber, or another suitable material, has a predetermined firmness. When measuring firmness (hardness) with a Shore durometer, the roller (25) has a firmness of between 10 shore A and 90 shore A. More preferably, the firmness of the roller (25) is between 20 shore A and 80 shore A. Most preferably, the firmness of the roller (25) is between 30 shore A and 60 shore A. The laminating roller (25) descends onto the release paper web (30) having the adhesive (20) and sandwiches the adhesive (20) between the release paper (30) and the film cover (10) while feathering the edges of the adhesive (20) to infinity creating a thin bordered edge (22) as can be seen in FIGS. 5A and 5B. The laminating roller (25), which is applied at a predetermined pressure, will deform and feather the edges based on thickness of the adhesive (20) on the release paper web (30). The resulting wound dressing or bandage (100) comprises the protective cover layer (10), the adhesive wafer comprising the adhesive (20) with a contoured edge, and the protective release paper sheet (30) as shown in FIGS. 5A and 5B. The edges of the dressing are feathered to infinity along the a to b and c to d plane as shown in FIG. 4. The web of formed bandages or dressings (100) is then driven (either pushed or pulled) to a cutting station, where it is cut into individual bandages then packaged.

The protective cover layer (10) may be any flexible polymeric film, such as polyurethane or polyethylene, or a woven or nonwoven fabric (porous or non-porous), or a layer of flexible polymeric foam (open cell or closed cell), or any other sheet material that is flexible, and preferably breathable, or a combination of such materials.

The adhesive wafers may be of any shape, including but not limited to round, oval, trapezoidal, or rectangular. The adhesive wafer and its resulting dressing may or may not have perforations.

The term "adhesive" in relation to wound dressings refers to any of a variety of materials in which a sticky, pliant adhesive composition constitutes a continuous phase and particles of one or more liquid-absorbing and swellable hydrocolloids are dispersed throughout the adhesive and constitute a discontinuous phase. Hydrocolloid adhesive compositions are well known in the art; however, a composition comprised of, as an example, at least one physically cross-linked elastomer selected from the group consisting of styrene-olefin-styrene block copolymer, butyl rubber and ethylene-propylene block copolymers, forming a continuous phase and at least one hydrocolloid dispersed therein, said hydrocolloid being selected from the group consisting of sodium carboxymethyl cellulose, pectin, gelatin, gaur gum, xantham gum, karaya gum, sodium polyacrylate and mixtures thereof, said compositions also containing at least one hydrocarbon tackifier selected from the group consisting of polymers and copolymers of alpha-pinene, beta-pinene, dicylopentadiene and also containing one or more hydrogenated esters of rosin. The adhesive (20) may be made more effective by incorporating antimicrobial substances such as silver salts and silver ceramic compounds. The adhesive (20) used in the present invention is preferably heated when deposited onto the release paper web. The heating may be accomplished by combining the components of the adhesive under heated conditions.

A machine for practicing the method of this invention comprises the horizontal lower platen member (40), a stationary upper platen member (50) having a gear pump station (15), the laminating roller (25) attached to the stationary upper platen member (50), a roller (35) or other suitable driving means that continuously moves the release paper web (30) forward. The gear pump (15) on the stationery upper platen (50) discontinuously deposits the adhesive (20) onto the continuously moving silicone release web (30) that is removably attached to the lower platen member (40). The laminating roller (25) carried by the upper platen member (50) descends onto the lower platen member (40) having the release paper (30) having the adhesive (20) and sandwiches it between the silicone release paper (30) and the film cover (10) and feathers the edges of the adhesive (20) to infinity creating a border edge (22) as shown in FIGS. 5A and 5B. The process forms a bandage or wound dressing (100) comprising the protective cover film (10), the adhesive wafer comprising the adhesive (20) and the release sheet (30). The web of formed bandage or dressing is then driven forward to a cutting station (60), where it is cut into individual bandages then packaged.

While the particular embodiments of the method have been shown above and described, it will be understood by those skilled in the arts that many of these details may be varied without departing from the spirit and scope of the invention.

I claim:

1. A method for making a contoured dressing, comprising the steps of:
   a. discontinuously depositing an adhesive in a specified shape and predetermined thickness using a gear pump onto a flexible silicone release web removably supported on an upper surface of a lower table member;
   b. laminating the deposited adhesive with a protective cover using a laminating roller with a predetermined softness and firmness to feather edges of the adhesive; and
   c. forming a contoured dressing having a center and a bordered edge.

2. The method of claim 1, wherein the roller has a firmness of between 10 shore A and 90 shore A.

3. The method of claim 2, wherein the roller has a firmness of between 20 shore A and 80 shore A.

4. The method of claim 3, wherein the roller has a firmness between 30 shore A and 60 shore A.

5. The method of claim 1, wherein the adhesive is comprised of at least one physically cross-linked elastomer selected from the group consisting of styrene-olefin-styrene block copolymer, butyl rubber and ethylene-propylene block copolymers, forming a continuous phase and at least one hydrocolloid dispersed therein, said hydrocolloid being selected from the group consisting of sodium carboxymethyl cellulose, pectin, gelatin, gaur gum, xantham gum, karaya gum, sodium polyacrylate and mixtures thereof, said adhesive also containing at least one hydrocarbon tackifier selected from the group consisting of polymers and copolymers of alpha-pinene, beta-pinene, dicylopentadiene and also containing one or more hydrogenated esters of rosin.

6. The method of claim 1, wherein the adhesive is heated.

7. The method of claim 1, wherein the protective cover is selected from the group consisting of polyurethane, polyethylene, a woven fabric, a nonwoven fabric, or a flexible polymeric foam.

8. The method of claim 1, wherein the adhesive is deposited in a shape selected from the group consisting of round, oval, trapezoidal, and rectangular.

9. The method of claim 1, wherein the adhesive is deposited with perforations.

10. The method of claim 1, further including the step of cutting and packaging the contoured dressing from the protective cover and the release web.

11. A method of forming a contoured dressing, comprising the steps of:
    a. discontinuously depositing an adhesive in a specified shape and predetermined thickness using a gear pump onto a flexible silicone release web removably supported on a lower horizontal platen member;
    b. laminating the deposited adhesive with a protective cover using a laminating roller with a predetermined softness and firmness to feather edges of the adhesive; and
    c. forming a contoured dressing having a center and a bordered edge.

12. The method of claim 11, wherein the adhesive comprised of at least one physically cross-linked elastomer selected from the group consisting of styrene-olefin-styrene block copolymer, butyl rubber and ethylene-propylene block copolymers, forming a continuous phase and at least one hydrocolloid dispersed therein, said hydrocolloid being selected from the group consisting of sodium carboxymethyl cellulose, pectin, gelatin, gaur gum, xantham gum, karaya gum, sodium polyacrylate and mixtures thereof, said adhesive also containing at least one hydrocarbon tackifier selected from the group consisting of polymers and copolymers of alpha-pinene, beta-pinene, dicylopentadiene and also containing one or more hydrogenated esters of rosin.

13. The method of claim 11, wherein the adhesive is heated.

14. The method of claim 11, wherein the protective cover is selected from the group consisting of polyurethane, polyethylene, a woven fabric, a nonwoven fabric, or a flexible polymeric foam.

15. The method of claim 11, wherein the adhesive is deposited in a shape selected from the group consisting of round, oval, trapezoidal, and rectangular.

16. The method of claim 11, wherein the adhesive is deposited with perforations.

17. The method of claim 11, wherein the roller has a firmness of between 10 shore A and 90 shore A.

18. The method of claim 11, further including the step of cutting and packaging the contoured dressing from the protective cover and the release web.

19. A method for making a contoured dressing, comprising the steps of:
    a. depositing an adhesive in a specified shape and predetermined thickness onto a flexible silicone release web, the depositing step consisting of using a gear pump to deposit the adhesive, wherein the release web is removably supported on an upper surface of a lower table member;
    b. laminating the deposited adhesive with a protective cover using a laminating roller with a predetermined softness and firmness to feather edges of the adhesive; and
    c. forming a contoured dressing having a center and a bordered edge.

20. The method of claim 19, further including the step of cutting and packaging the contoured dressing from the protective cover and the release web.

* * * * *